(12) United States Patent
Kelsey et al.

(10) Patent No.: US 7,180,302 B2
(45) Date of Patent: Feb. 20, 2007

(54) METHOD AND SYSTEM FOR DETERMINING CRACKS AND BROKEN COMPONENTS IN ARMOR

(75) Inventors: P. Victor Kelsey, Chandler, AZ (US); F. Stanton Lyons, Phoenix, AZ (US); Marvin Kent Richards, Gilbert, AZ (US); Curtis P. Parsons, Chandler, AZ (US); Donnie L. Bowser, Chandler, AZ (US); Michael F. Daly, Phoenix, AZ (US)

(73) Assignee: Simula, Inc, Phoenix, AZ (US)

( * ) Notice: Subject to any disclaimer, the term of this patent is extended or adjusted under 35 U.S.C. 154(b) by 0 days.

(21) Appl. No.: 10/892,357

(22) Filed: Jul. 16, 2004

(65) Prior Publication Data

US 2006/0012375 A1 Jan. 19, 2006

(51) Int. Cl.
*G01R 31/08* (2006.01)
(52) U.S. Cl. ............... 324/525; 324/691; 324/693; 73/799
(58) Field of Classification Search ............ 324/525; 2/905; 73/799
See application file for complete search history.

(56) References Cited

U.S. PATENT DOCUMENTS

| | | | | |
|---|---|---|---|---|
| 3,596,269 A | * | 7/1971 | Laska | 340/518 |
| 4,255,974 A | * | 3/1981 | Dufrane et al. | 73/776 |
| 4,419,889 A | * | 12/1983 | Muto et al. | 73/335.02 |
| 4,503,710 A | | 3/1985 | Oertle et al. | |
| 4,546,652 A | * | 10/1985 | Virkar et al. | 73/776 |
| 4,621,249 A | * | 11/1986 | Uchikawa et al. | 338/35 |
| 4,679,961 A | * | 7/1987 | Stewart | 403/341 |
| 4,918,377 A | * | 4/1990 | Buehler et al. | 324/691 |
| 5,060,553 A | * | 10/1991 | Jones | 89/36.02 |
| 5,214,387 A | | 5/1993 | Fenner | |
| 5,378,991 A | | 1/1995 | Anderson et al. | |
| 5,395,641 A | * | 3/1995 | Shibata et al. | 427/8 |
| 5,554,816 A | * | 9/1996 | Skaggs et al. | 89/36.17 |
| 5,560,851 A | * | 10/1996 | Thimm et al. | 219/543 |
| 5,636,378 A | * | 6/1997 | Griffith | 2/455 |
| 5,906,004 A | | 5/1999 | Lebby et al. | |
| 5,969,532 A | | 10/1999 | Usui et al. | |
| 6,268,717 B1 | * | 7/2001 | Jarvis et al. | 324/158.1 |
| 6,408,733 B1 | | 6/2002 | Perciballi | |

(Continued)

OTHER PUBLICATIONS

"Acoustic Techniques for the Inspection of Ballistic Protective Inserts in Personnel Armor", Sample Journal, Sep./Oct. 2003, p. 1-8.

(Continued)

*Primary Examiner*—Andrew H. Hirshfeld
*Assistant Examiner*—John Zhu
(74) *Attorney, Agent, or Firm*—Paul Hastings Janofsky & Walker, LLP; Aslan Baghdadi

(57) ABSTRACT

A ceramic armor system with built-in conductive circuit attached to a ceramic component. The conductive circuit can be accessed by a user at contacts provided in the system. The circuit is arranged so that damage such as cracks that occurs within the ceramic component can propagate into the conductive material forming the circuit and thereby cause a rupture in the conductive circuit. An electrical probe such as an ohmmeter is used to measure the conductive circuit resistance that is then checked against an expected value. The results are used to determine if the ceramic armor component is in operable condition.

15 Claims, 18 Drawing Sheets

U.S. PATENT DOCUMENTS 6,802,216 B2 * 10/2004 van Schoor et al. .......... 73/159
6,893,271 B2 *  5/2005 Seith et al. ................... 439/79

OTHER PUBLICATIONS

"Real-Time X-ray Technology for Inspecting Critical Devices", Medical Electronics Manufacturing, Fall 2003.

"Non-Destructive Inspectin of Future Combat Systems", Proceedings of the 23rd Army Science Conference, 2002.

"Innovative Concepts for the Performance & Quality Assurance of Ceramic Title Armor Systems", 11th Annual US Army Ground Vehicle Survivability Symposium, Mar. 27-30, 2000.

Search Report for International Application No. PCT/US05/24859, dated Apr. 7, 2006.

Written Opinion for International Application No. PCT/US05/24859, dated Apr. 7, 2006.

* cited by examiner

METHOD AND SYSTEM FOR DETERMINING CRACKS AND BROKEN COMPONENTS IN ARMOR

BACKGROUND

1. Field of the Invention

The present invention relates generally to armor systems and in particular to a method for determining the presence of cracks and other broken components in a piece of armor.

2. Background of the Invention

Many high performance armor systems contain ceramic components that are subject to cracking and fracture during normal operations in the field. Cracks form readily due to the brittle nature of ceramic materials, including a low fracture toughness. Furthermore, a cracked component will not exhibit the same tensile or compressive strength as a pristine, undamaged component. Thus, a cracked ceramic component may serve to compromise the ballistic integrity of an armor system in which it is embedded, particularly for impacts near the crack or damaged region. The problem is compounded by the fact that when a ceramic component is embedded in a system, such as an armor system, it may be virtually inaccessible to visual inspection to detect cracks or other damage.

Traditional methods for determination of crack formation in a ceramic body, over and above visual inspection, include X-ray or ultrasonic detection methods, as taught in, for example, "Acoustic Techniques for the Inspection of ballistic Protective Inserts in Personnel Armor," SAMPE Journal, September/October, 2003, pp. 1–8. Both of the latter techniques, while useful in a laboratory setting, are much less practical in a "field" setting, such as a combat area, due to their lack of portability. Other techniques for detection of cracks in ceramics include electrical measurement of a ceramic with one surface immersed in a conductive liquid, as taught in U.S. Pat. No. 5,969,532 to Usui. The latter technique, however, may not lend itself to use in "field" settings where immersion of a ceramic in a liquid may not be feasible.

In light of the above discussion, it will be appreciated that a need exists for improvements in detecting defects in a convenient manner in ceramic and related systems.

BRIEF SUMMARY

An embodiment of the present invention includes a ceramic armor system with a built-in electrical circuit for detecting defects such as cracks within a ceramic body contained in the system. The ceramic armor system may include one or more ceramic pieces. The ceramic pieces may be contained or attached to an additional armor element such as a fiber reinforced composite. Preferably, affixed to each ceramic piece is a conductive circuit that can be connected to or probed with external conductors for measuring the resistance of the circuit. In exemplary embodiments, the ceramic pieces are shaped as tiles (or "plates") and have a conductive circuit affixed to one or both large flat surfaces. A crack in the armor system that propagates through the ceramic and breaks the conductive circuit attached to the ceramic in the region of the crack, results in the circuit displaying an infinite, or "open" resistance. Accordingly, an electrical measurement performed by, for example, a portable hand-held electrical device, can be conveniently conducted in the field to assess the presence of a crack or related damage in the armor system.

In another embodiment of the present invention, a method for detection of damage in a ceramic system includes a step of fabricating a ceramic body ("component") and a conductive circuit that adheres to a surface of the ceramic body to be housed in the system. The conductive circuit may be fabricated in one of a variety of configurations, but will have at least two contacts connected to different parts of the circuit that can be accessed by an external measuring device. The circuit may include elements such as electrical resistors. In an additional step, one or more ceramics, each with an attached conductive circuit, are affixed to or within a housing. In a further step, electrical conductors are placed in contact with two contacts connected to a conductive circuit attached to a ceramic body so that the conductive circuit resistance can be probed. The conductors may be connected to an ohmmeter, voltage measuring device, LED, or other device that can be used to measure the electrical conductivity of the attached conductive circuit. The measured resistance is checked against an expected resistance, in order to establish whether the ceramic remains substantially undamaged, or whether it contains cracks or other defects sufficient to break the conductive circuit.

In a further embodiment of the present invention, a ceramic system that can be field tested for damage includes a means for housing one or more ceramic pieces. The housing means could be made of, among other materials, a metal, a reinforced composite, or a polymer cloth. The system additionally includes a damage-signaling means that is attached to a ceramic piece housed in the system. The damage-signaling means could include a wire, a screened ink pattern, a lithographic circuit, or other electrical pattern that can be attached to the ceramic piece. Also included in the system is an access means for accessing the damage-signaling means. In some embodiments the access means includes a pair of contact pads each attached to the damage-signaling means, and probable by a variety of electrical measuring devices. In other embodiments, the access means includes an enclosed connector configured to accept a standard electrical probe.

BRIEF DESCRIPTION OF THE DRAWINGS

FIG. 1b is a schematic diagram illustrating crack formation in the armor system with a built-in circuit for crack detection of FIG. 1a.

FIG. 8b is a schematic diagram illustrating the effect of a conductive defect on the measurement of the circuit of FIG. 8a.

DETAILED DESCRIPTION OF THE PREFERRED EMBODIMENTS OF THE INVENTION

Figure 1A:
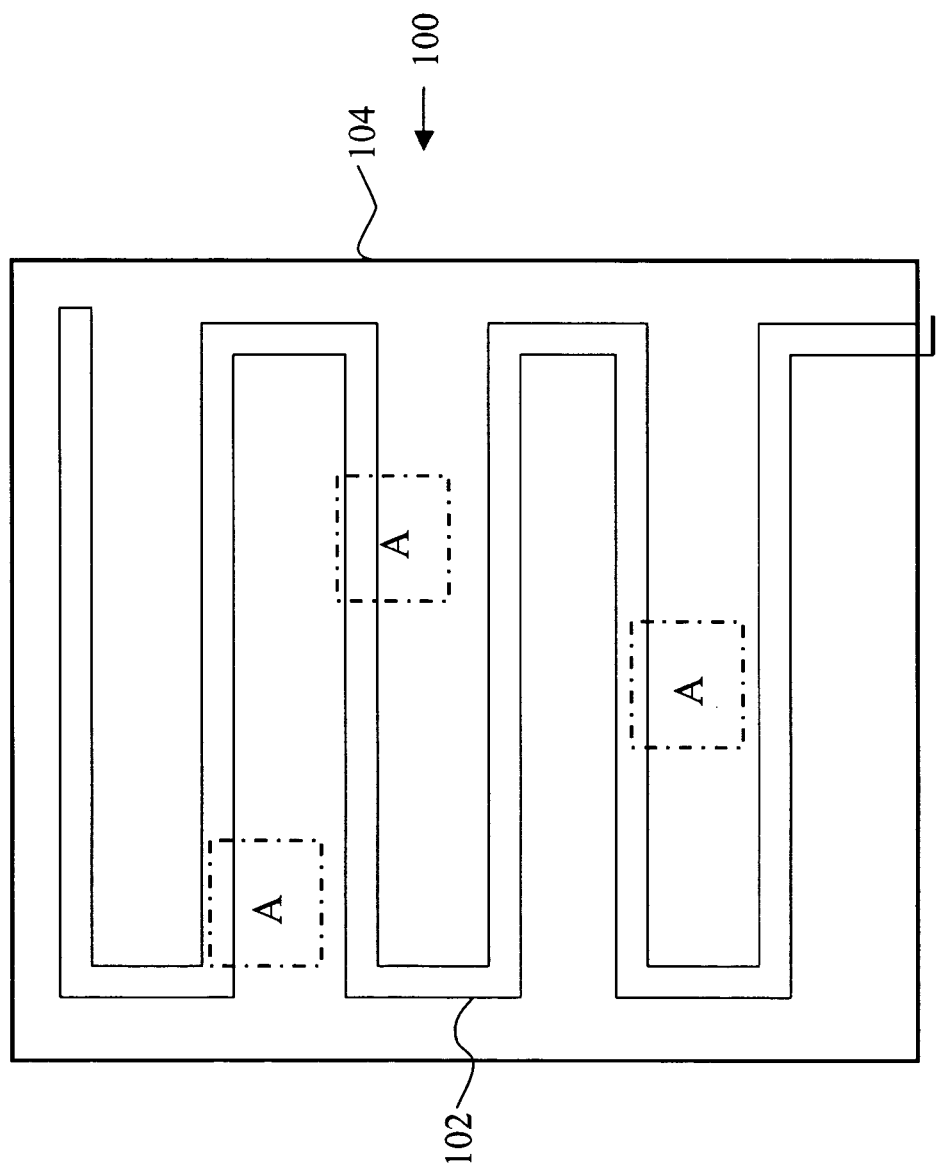
FIG. 1a is a schematic diagram illustrating an armor system with a built-in circuit for crack detection according to an exemplary embodiment of the present invention.

FIG. 1a is a schematic diagram illustrating features of a ceramic armor system 100 with a built-in electrical circuit 102 used for defect detection, according to an exemplary embodiment of the present invention. An armor piece having a ceramic body 104 (also referred to as "component") to be included in the system may assume any shape. In a preferred embodiment, the ceramic component has the proportions of a flat object such as a tile. In exemplary embodiments, the ceramic component is made essentially of ceramic material. In other embodiments, the ceramic component may be a ceramic composite of known composition and microstructure. In preferred embodiments, the ceramic component is designed to be housed in an armor system and act as protection against ballistic impact. Circuit 102 is affixed to component 104 such that it adheres to a surface of the component. For example, circuit 102 may be formed from a conductive ink applied to a surface of component 104.

The layout of circuit 102 is such that the conductive path, although narrow, exhibits substantial electrical coverage of component 104. The term "substantial electrical coverage" is meant to indicate that there are no large areas on the ceramic surface in which a portion of circuit 102 does not contact. As shown in FIG. 1a, a square area of dimensions larger than "A" will be contacted at some point by circuit 102. Thus, as depicted in FIG. 1b, randomly oriented linear cracks 106 of dimensions as shown will have a high probability of intersecting the region of the ceramic affixed to circuit 102 at some point.

When crack 106 forms in ceramic 104, it may propagate throughout the thickness of the ceramic. The "thickness" of ceramic 104 is defined as the short distance, $\tau$, as shown in FIG. 1c. FIG. 1c is a schematic diagram illustrating a cross-section of ceramic component 104 along B–B' in FIG. 1b. In a preferred embodiment, circuit 102 is fabricated from a material with low tensile strength, such that when any crack 106 propagates through the thickness of the ceramic at a point above conductor 102, a rupture in conductor 102 is induced. Thus, cracks extending through the thickness of the ceramic whose length exceeds a certain threshold, will likely encounter the circuit and cause a rupture in circuit 102. Once ruptured, the electrical resistance of circuit 102 will be significantly altered, such that an electrical measurement applied to circuit 102 will signal that ceramic component 104 has been damaged.

Figure 1B:
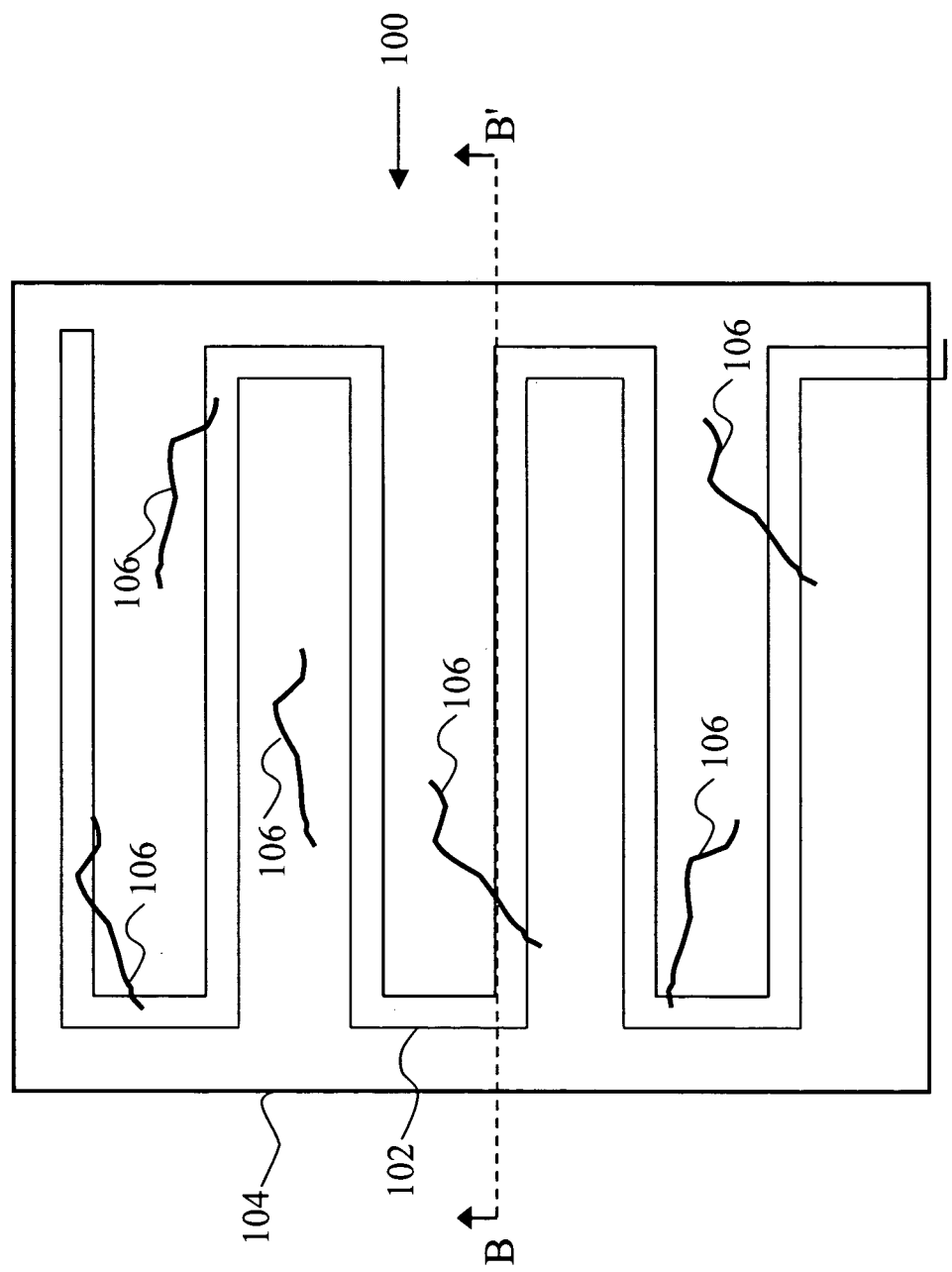
Figure 1C:
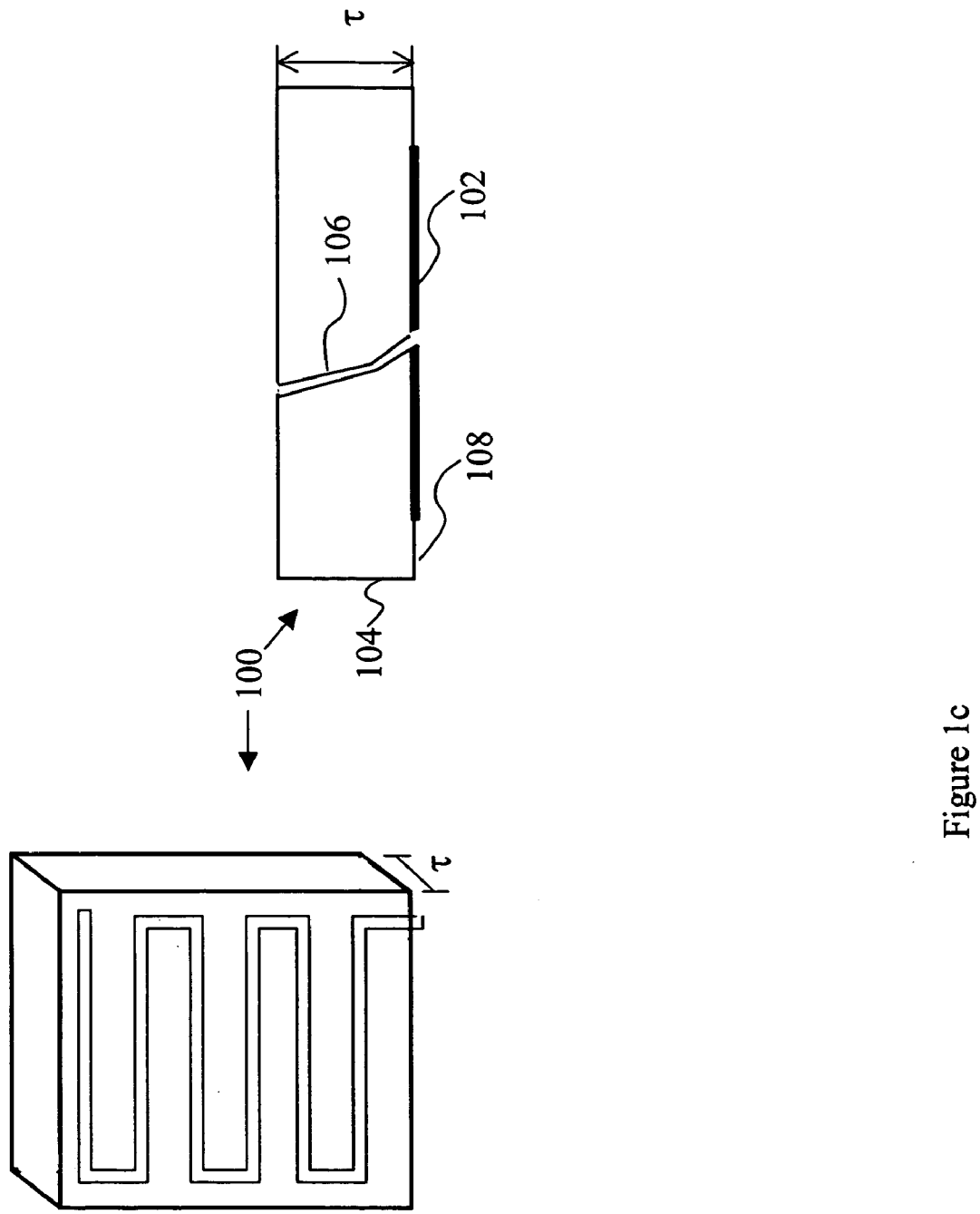
FIG. 1c is a schematic diagram illustrating a cross-section of the ceramic component depicted in FIG. 1b.
Figure 1D:
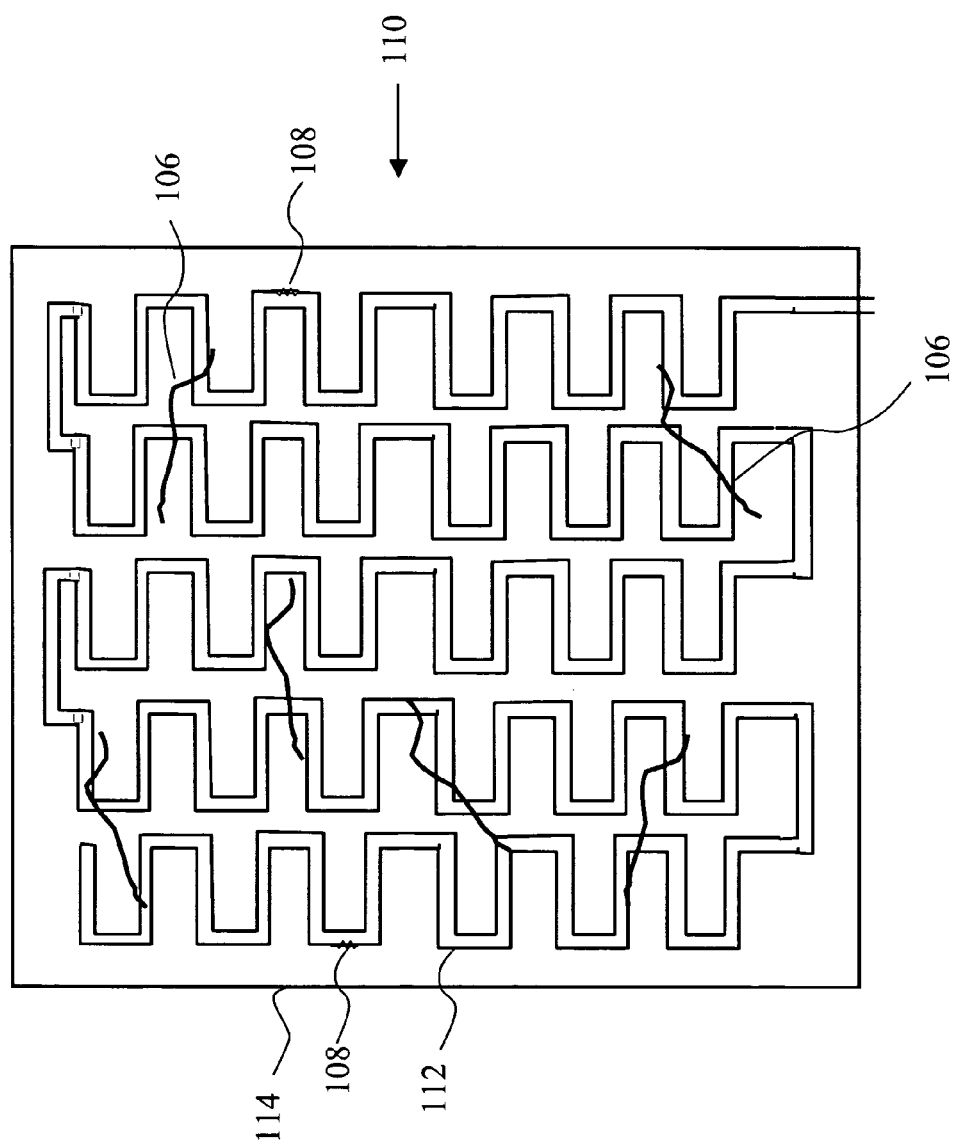
FIG. 1d is a schematic diagram illustrating an armor system with a built-in circuit for crack detection according to another exemplary embodiment of the present invention.

As depicted in FIG. 1b, circuit 102 may fail to intersect some cracks 106 that might form within component 104. Depending on the length and orientation of the crack, it may lie within a region not contacted by circuit 102. However, in embodiments of the present invention, the circuit can be arranged with an appropriate pattern that has a broader coverage, as depicted in FIG. 1d, such that any cracks longer than a desired dimension can be detected. System 110 includes ceramic 114 and circuit 112, which now intersects all cracks 106. Thus, system 110, by incorporating an electrical circuit that is broken when a ceramic crack intersects the circuit, provides a robust means to signal a user as to the presence of damage to the ceramic component that could be deleterious to the operation of the component as a protective armor piece. Also included in circuit 112 are resistors 108, which can further aid in diagnosis of damage to the ceramic as discussed further below with respect to FIG. 8.

Figure 2:
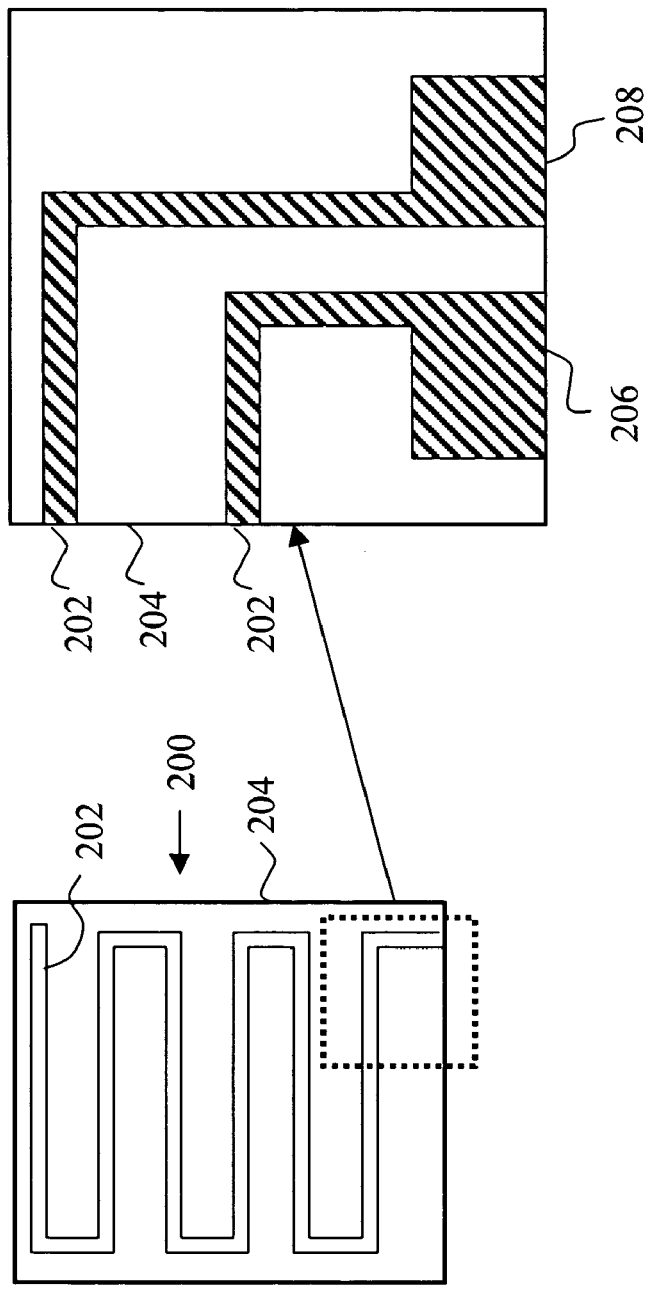
FIG. 2 is a schematic diagram depicting details of a ceramic armor system with built-in defect detection according to another embodiment of the present invention.

FIG. 2 is a schematic diagram illustrating further details of a ceramic armor system 200 with built-in defect detection according to another embodiment of the present invention. Circuit 202 is terminated on different ends by pads 206 and 208. Pads 206 and 208, whose size is much larger than the width of the circuit "wire," provide a convenient means to measure the circuit resistance using electrical probes or similar devices to contact the pads. Circuit 202 and pads 206, 208 may be fabricated by any appropriate method known to those skilled in the art. For example, circuit 202 may be formed using a patterned conductive ink or paste. Alternatively, circuit 202 may comprise metal wires that are terminated in metallic pads.

Figure 3:
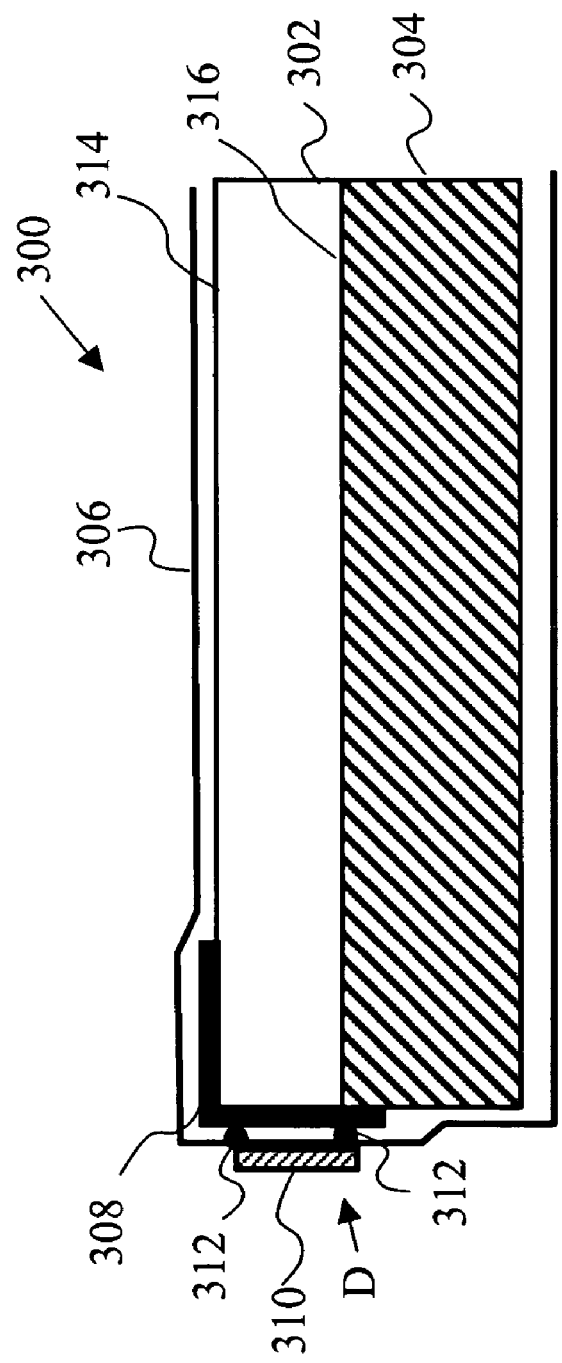
FIG. 3 is a schematic diagram illustrating details of a side contact for contacting a ceramic armor system according to an additional exemplary embodiment of the present invention.

FIG. 3 is a schematic diagram illustrating a cross-section of a ceramic armor system 300 including a ceramic component 302, backing 304, and cover 306. In an exemplary embodiment of the present invention, backing 304 (also referred to as a "backing plate") contains a fiber reinforced composite material. In exemplary embodiments, cover 306 is a cloth material formed from nylon or similar fibers. In system 300, conducting pad 308 extends from the top surface of ceramic 302 and runs along the side of component 302 and backing 304, forming a side surface contact. In this manner, measurements at point D can be performed without having to expose the top of the ceramic. Preferably, pad 308 is a metal foil. In an exemplary embodiment, removable inspection sticker 310 is placed over an opening in cover 306 located above a portion of pad 308. Preferably, an elastomeric seal 312 joins cover 306 and connecting pad 308, providing environmental protection of the armor materials.

Referring now to FIGS. 1a and 3, in a preferred embodiment of the present invention, a circuit such as circuit 102 is attached to the back surface of ceramic 104. That is, circuit 102 lies on an inner ("back") ceramic surface attached to a backing, as for example, surface 316 depicted in FIG. 3. When disposed on the back surface of the ceramic, a circuit such as circuit 102 is substantially protected from environmental degradation. In other embodiments, a circuit such as circuit 102 is attached to the ceramic front surface, depicted, for example as surface 314 in FIG. 3. An advantage of the latter arrangement is that the circuit may be attached after the ceramic is bonded or otherwise attached to a backing plate, such as plate 304. Accordingly, the circuit is not exposed to processing conditions, such as high temperatures that may be used to bond and treat the ceramic and backing plate. This potentially affords a greater choice of materials from which to select for circuit fabrication. Alternatively, crack detection circuits may be attached to both surfaces of a ceramic, or more than one circuit may be attached to one or both of front and back surfaces to incorporate redundancy into the system.

Figure 4:
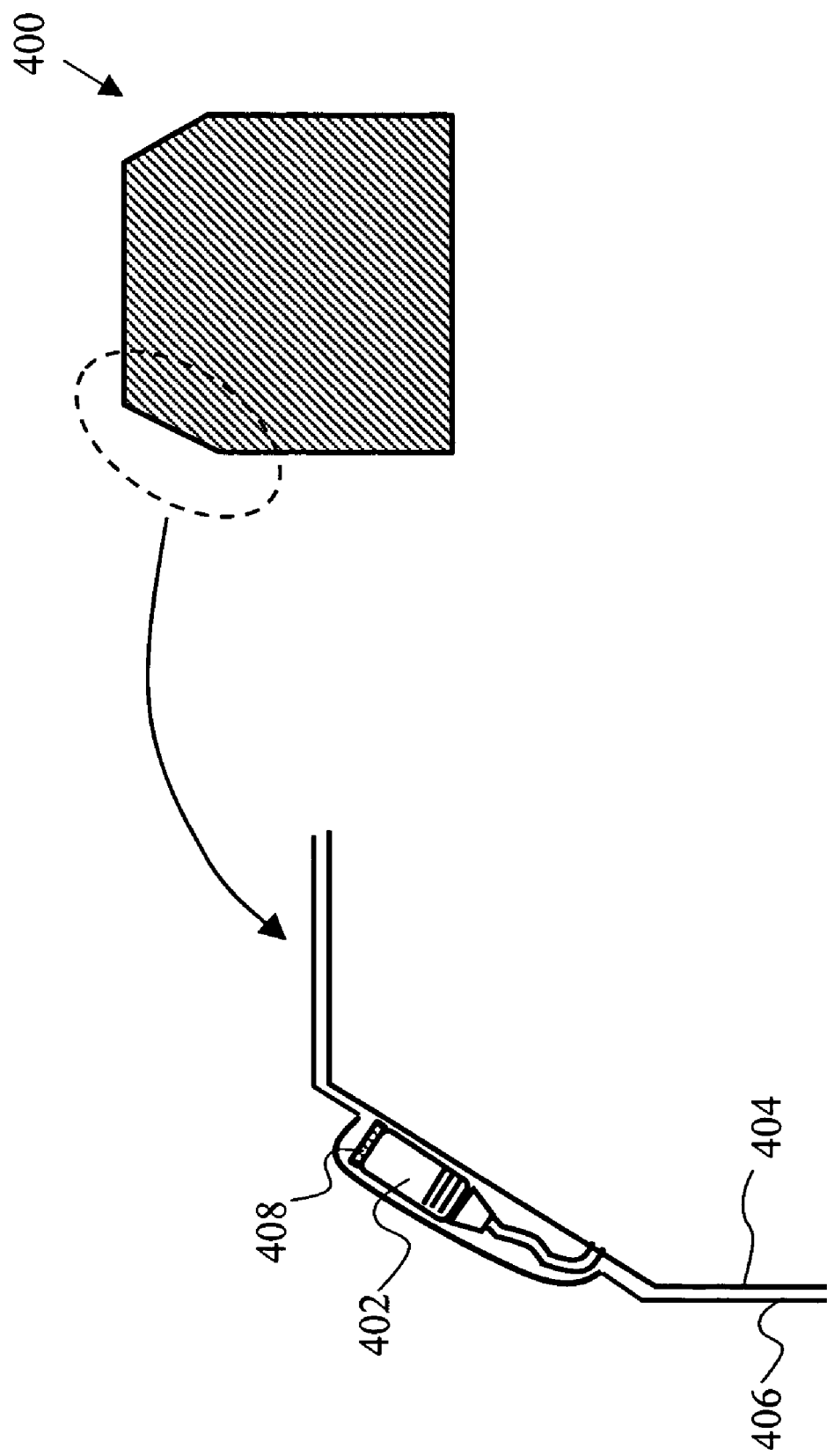
FIG. 4 is a schematic diagram illustrating details of an integrated connector for contacting a ceramic armor system according to an exemplary embodiment of the present invention.

In another embodiment of the present invention, depicted in FIG. 4, system 400 includes an integrated electrical connector 402. Preferably, connector 402 is integrated at an edge of system 400. Connector 402 may be placed, for example, underneath cover 406 that covers ceramic 404. Connector 402 may be configured in one of several forms convenient for coupling to known electrical probes. Preferably, connector 402 contacts two ends of a circuit (not shown) embedded in system 400, and contains two contact points extending toward the outside, such that the circuit resistance can be measured by plugging probes into connector 402. Optional cap 408 may be placed on connector 402 when not in use. An opening (not shown) in cover 406 may be used to provide convenient access to connector 402.

Figure 5:
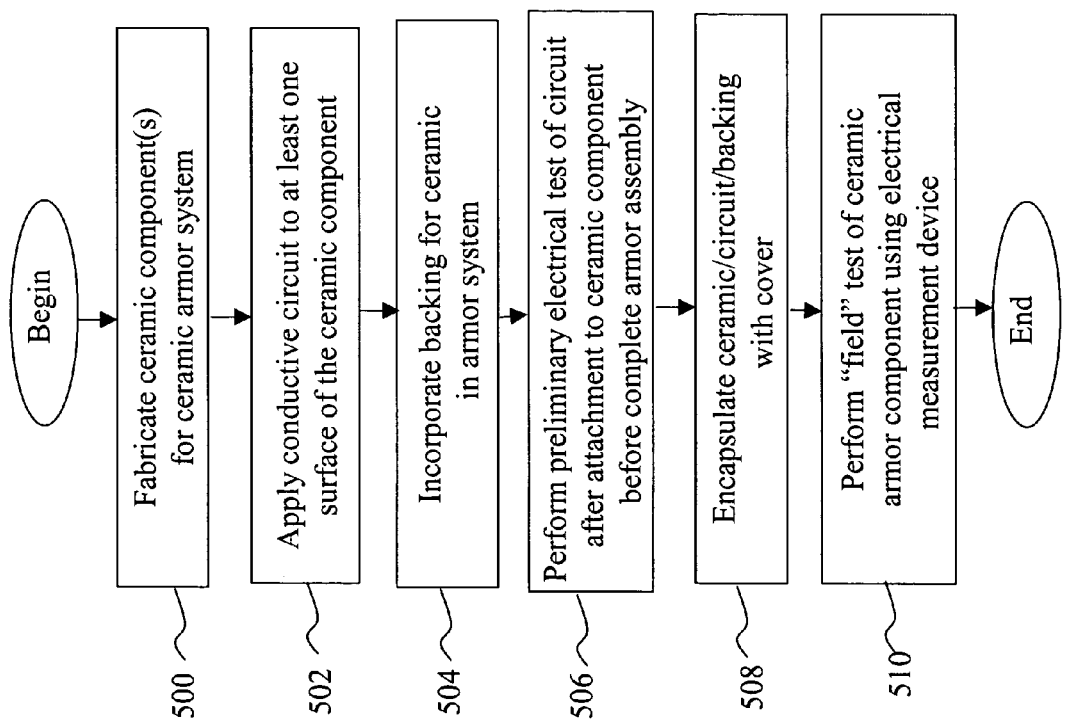
FIG. 5 illustrates exemplary steps for "field" detection of ceramic armor defects according to an exemplary embodiment of the present invention.

In an exemplary embodiment of the present invention depicted in FIG. 5, a process for "field" detection of ceramic armor defects includes step 500, when a ceramic component to be housed in a ceramic armor system is fabricated. The ceramic may be specially prepared to accept an electrical circuit to be attached thereto. In a preferred embodiment, the ceramic component is a conventional component that could otherwise be used without modification in a conventional armor system.

In step 502, a conductive circuit is applied to at least one surface of the ceramic component. The term "applied" denotes that the circuit is made to adhere to the ceramic component. For ceramic components that are plate-like in nature, the circuit can be applied to the "top" or "bottom" of the plate.

After the conductive circuit is applied to the ceramic component, the ceramic component may be incorporated in a system designed to house the ceramic component, as a part of a ceramic armor system, for example. Incorporation in the system may proceed by first applying a backing to the ceramic component, and may include further steps of housing the ceramic component within a cover. In optional step 504, a backing for the ceramic component with attached conductive circuit is incorporated into the system. The backing may contain a fiber reinforced composite of known material and structure used in ceramic armor systems. As noted above, the mounting of the ceramic to a backing may be performed before or after the attaching of the electrical circuit to the ceramic. In other words, in embodiments of the present invention, step 502 is alternatively performed before or after some or all portions of step 504. An example of a known processes that can be implemented in step 504 is thermal pressing of a fiber-reinforced composite used as a backing plate material.

In optional step 506, a preliminary electrical test measurement of the electrical circuit attached to the ceramic component is performed. This provides a screening process to allow defective parts to be detected before complete assembly within the ceramic system, for example, before an outer cover is placed on the ceramic/circuit attached to the backing. In cases where the electrical circuit is attached to the ceramic component before a backing plate is introduced into the system, step 506 may be performed before, after, or both before and after, the backing plate is incorporated in the system.

In optional step 508, a cover such as a nylon cloth is applied to encapsulate the ceramic and backing component. Preferably, though not necessarily, the cover includes at least one opening for a probe or probes to contact the electrical circuit. In an exemplary embodiment of the present invention, the outer surface of the cover is marked to indicate locations where the circuit can be contacted, for example, the location of contact pad(s) 308. Thus, electrical measurements can be subsequently conducted without unduly disturbing the ceramic armor system because an operator knows where to place an electrical probe. Optionally, operations in step 508 may be incorporated in step 504.

In step 510, a user performs a "field" test of the system by applying electrical probes connected to a measuring device to contacts connected to one or more electrical circuits that are attached to the ceramic armor system. The probes may be applied through specially designed openings in a cover, through pores in a cloth cover, or to an uncovered ceramic component. The field test is performed after the ceramic armor system has been fully assembled and optionally deployed for use. If the circuit resistance measured is in accordance with an expected value, the value may be recorded and the ceramic armor system is deemed in operable condition with respect to cracks and related damage. If the circuit does not exhibit the expected value, depending on the nature of the reading, as discussed further below, the ceramic may be deemed cracked and in need of replacement, if possible. The armor system may then, for example, be temporarily or permanently removed from use.

Figure 6:
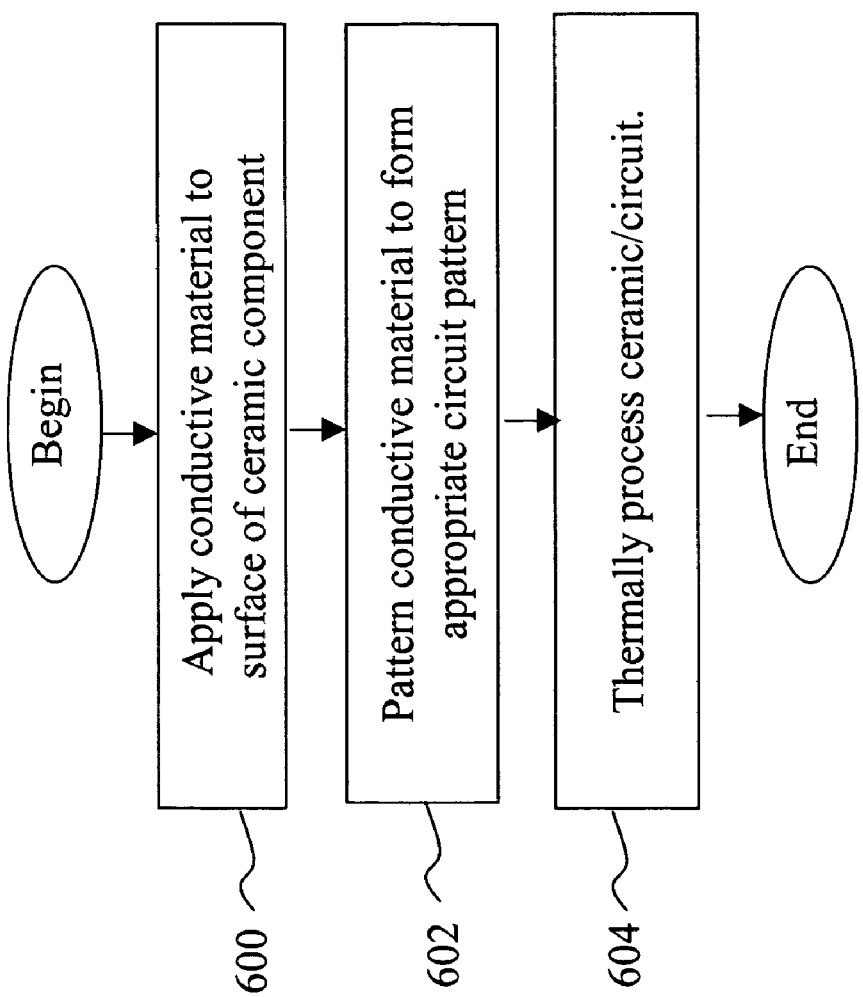
FIG. 6 illustrates additional details of the process illustrated in FIG. 5.

FIG. 6 illustrates details of step 502 according to an exemplary embodiment of the present invention. Referring also to FIG. 1c, in step 600, a conductive material (not shown) is applied to a surface of a ceramic body, such as surface 108.

In step 602, the conductive material is patterned to form a pattern such as that depicted for circuit 102 in FIG. 1a. Patterning may be accomplished by known methods such as photolithography, photodeposition, and screen printing, for example. Alternatively, patterning of a metal wire applied to a ceramic surface may include arranging and bonding the wire to the ceramic surface according to a predetermined layout.

In optional step 604, the conductive circuit material disposed on the ceramic is thermally processed. This may be useful, for example, to drive out volatile components of a conductive material precursor, and/or to improve the circuit conductivity.

Figure 7:
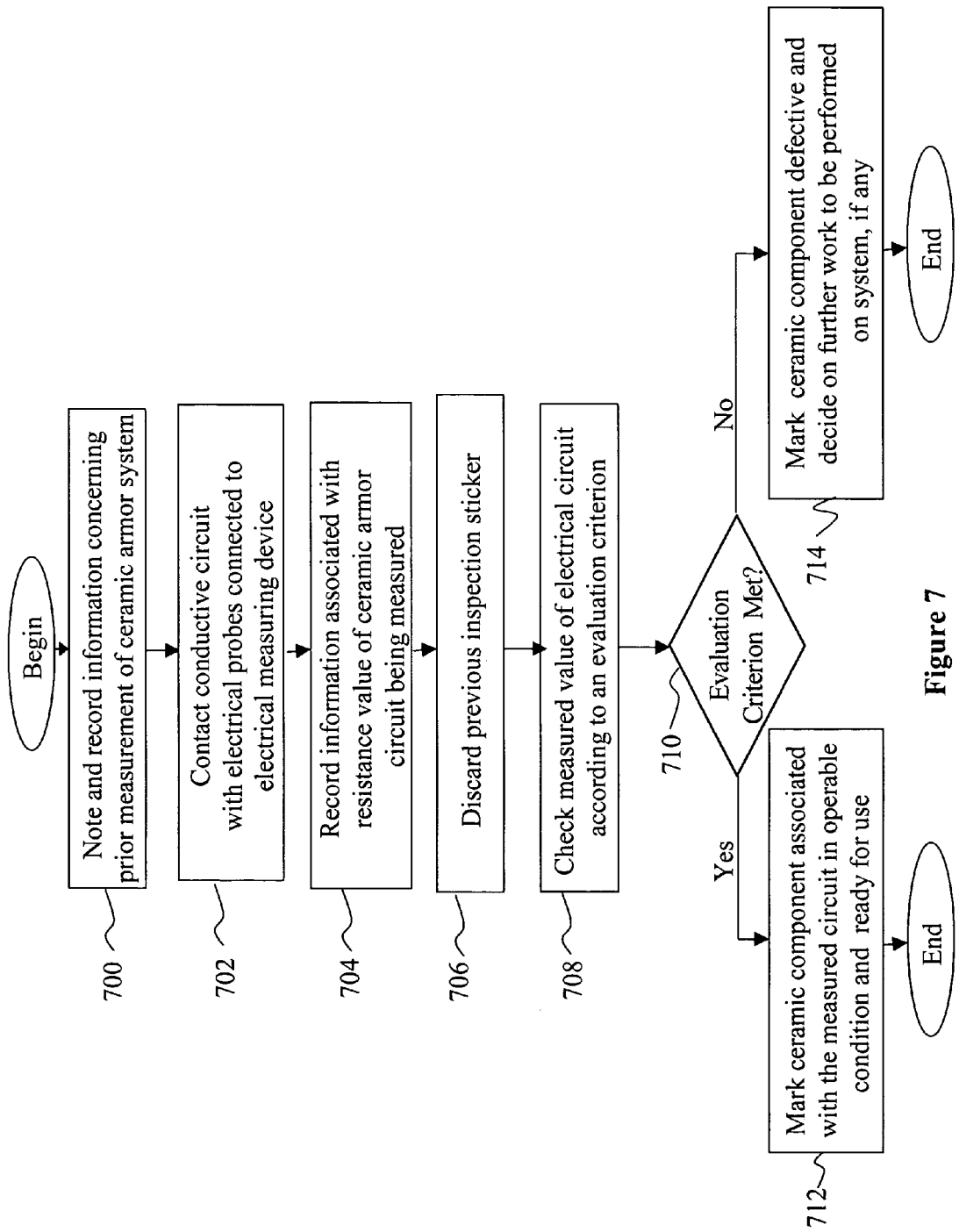
FIG. 7 illustrates still further details of the process of FIG. 5.

FIG. 7 illustrates details of step 508 according to an exemplary embodiment of the present invention. In optional step 700, information concerning a previous measurement of the ceramic armor system is noted and/or recorded. The information may be contained in an inspection sticker affixed to the ceramic armor system in proximity to the contact point used for the measurement. The information may include a measurement date, resistance value, and brief comments.

In step 702, a user contacts a conducting circuit with electrical probes connected to an electrical measuring device, such as a hand-held ohmmeter. Contacting may be performed, for example, by placing probes on contact pads, or placing probes within an electrical connector or connectors configured to accept known electrical probes. Measurement may be performed by setting a measuring device to "resistance" mode, which displays the electrical resistance of the circuit being measured, for instance, the DC resistance.

In step 704, information associated with the resistance value of the ceramic armor circuit being measured is recorded. Examples of information associated with the measurement are resistance value, date of measurement, last measurement resistance value, and comments. In an exemplary embodiment, the resistance measurement information is recorded on a new inspection sticker attached to the system. The inspection sticker may, for example, be configured as element 310 in FIG. 3, to cover a circuit contact point. Alternatively, a sticker may be placed on an outside surface of a cover in the vicinity of a circuit contact point residing underneath the cover.

In optional step 706, a previous inspection sticker is discarded so that the new inspection sticker may reside in place of the previous one. For example, sticker 310 may be replaced with an updated sticker each time a measurement is performed at contact 308. The updated sticker may nonetheless include information from the previous inspection sticker to facilitate tracking of the armor measurement history.

In step 708, the measured value of the electrical circuit is checked according to an evaluation criterion to determine whether the armor system is in proper condition. The evaluation criterion may include comparison to a previously measured resistance value, if available, and/or to an expected resistance value.

The process moves to step 710 where, if the criterion is met, then in step 712, the ceramic component associated with the measured circuit is marked in operable condition. It may then be returned to field operation as necessary.

If the criterion is not met, the process moves to step 714. In step 714, a user notes a potential ceramic armor fail and decides whether the component or system needs further evaluation, component replacement, or discarding.

Figure 8A:
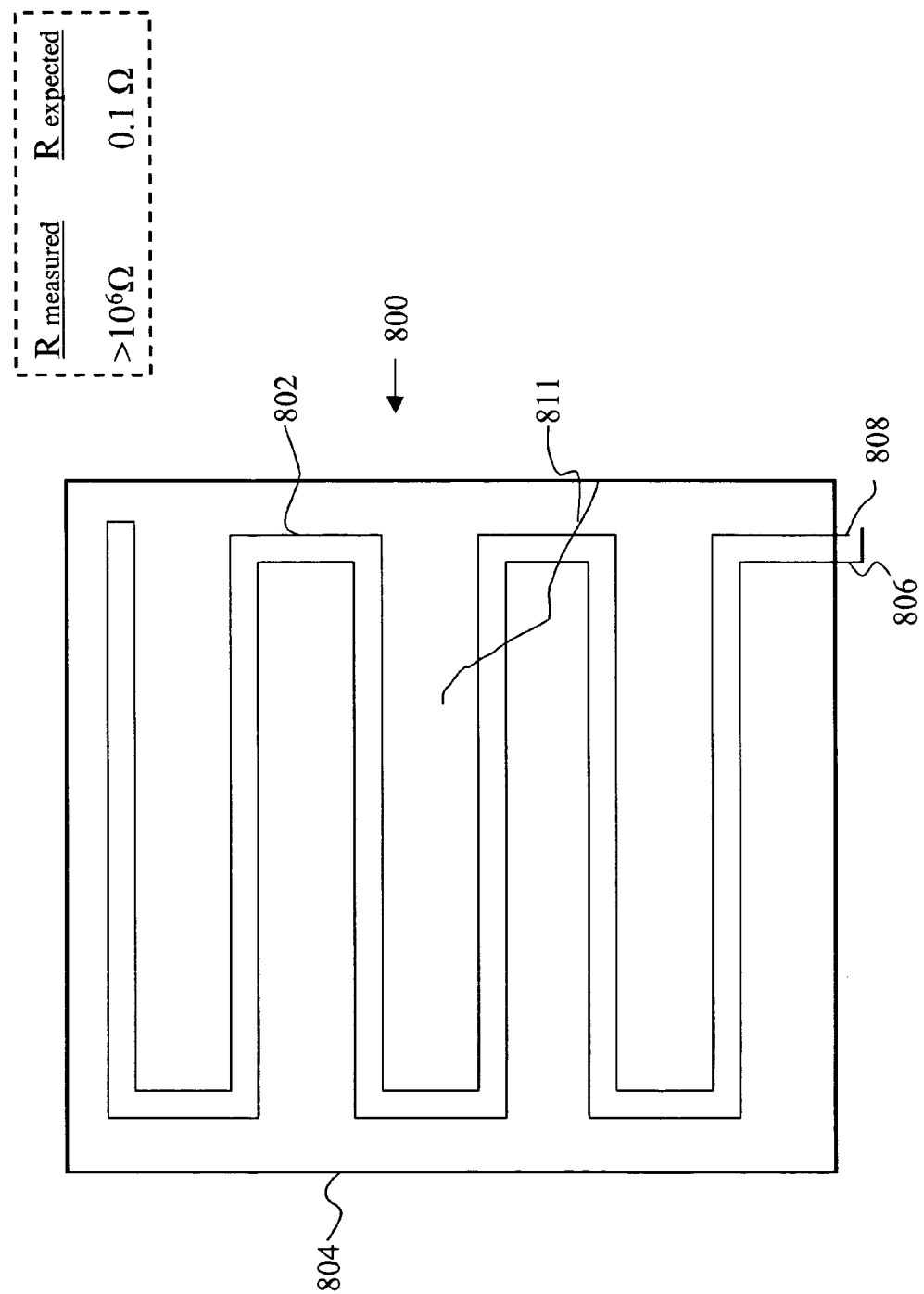
FIG. 8a is a schematic diagram depicting a circuit for crack detection in a ceramic armor according to an exemplary embodiment of the present invention.

FIGS. 8a–8g further illustrate operation of a ceramic armor system according to additional embodiments of the present invention. In FIG. 8a, system 800 includes circuit 802 with ends 806 and 808. In the example shown, the circuit resistance as designed is expected to be about 0.1 Ω. A crack 811 that initiates a rupture in circuit 802 will cause an electrical measuring device to register a very high resistance (typically>$10^6$ Ω) or "open," thus signaling damage in the ceramic.

Figure 8B:
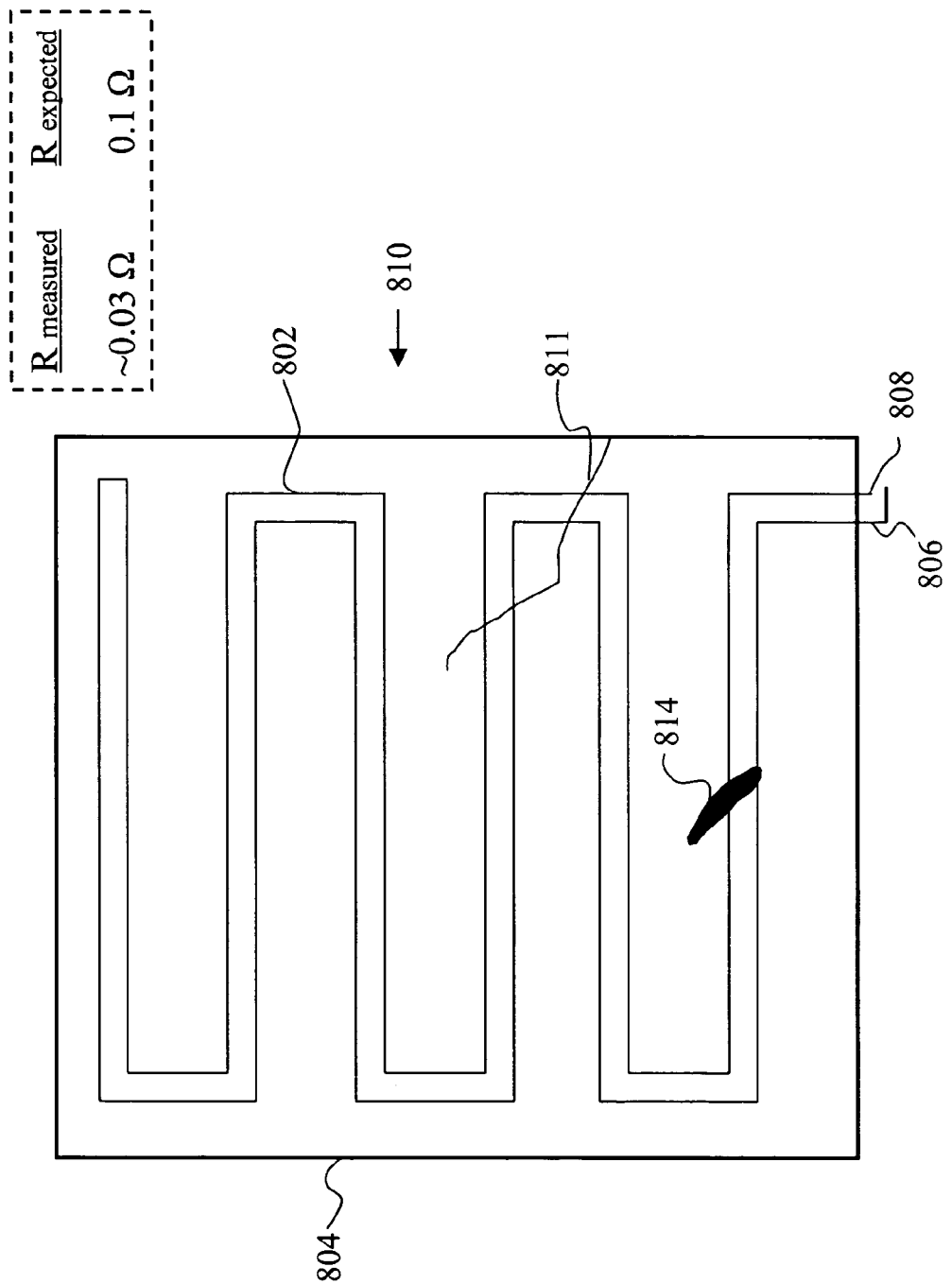

In FIG. 8b, circuit 802 includes an electrically conducting defect 814 inadvertently incorporated in circuit 802. For example, during processing an extraneous portion of electrical conductor may become located on the ceramic surface containing the circuit. This may result from incomplete removal or inadvertent placement of conductive material in regions of the ceramic surface designed to be free of conductive matter. Moreover, in preferred embodiments where the circuit resides on the back surface of the ceramic component, after a backing is applied to the ceramic, any residual extraneous conductive material will be undetectable to visual inspection. The location of defect 814 causes a short circuit between points 806, 814, 808. The measured resistance of this short circuit will be a fraction of the full circuit resistance of undamaged circuit 802, perhaps about 0.03 Ω. However, a user measuring system 810 will likely fail to ascribe the discrepancy between measured value and expected value to any problem within the circuit, inasmuch as the expected full circuit resistance value is only about 0.1 Ω, and typical ohmmeters used to perform such measurements may have a measurement uncertainty greater than the discrepancy. Accordingly, after recording such a measurement, a user may be falsely under the impression that the system is in proper working order. If a crack 811 is present in the location indicated, its presence will not be detected, since the circuit 802 is severed by the crack at a point beyond the short circuiting point. Therefore, system 810 is susceptible to providing "false negative" results, in which cracks or related damage may go undetected by an apparently normal resistance measurement.

In exemplary embodiments of the present invention, resistors are included in conductive circuits to help, among other things, reduce the problem of false negative measurements. In the exemplary embodiment illustrated in FIG. 8c, system 820 includes resistor 812, in series with the rest of circuit 822. Preferably, resistor 812 has substantially higher resistance than the series resistance imparted by the remainder of the circuit 822 ("residual circuit resistance"). For example, if the residual circuit resistance is in the range of about 0.1–1.0 Ω, in preferred embodiments, the resistance of resistor 812 is equal to or greater than about 10 Ω. In cases where the residual circuit resistance is, for example, about 10 Ω, a preferable resistance range for resistor 812 corresponds to about 50 Ω or greater. Because resistors such as resistor 812 are generally stable and have reproducible resistance values, the inclusion of resistor 812 in circuit 822 aids a user wishing to measure the circuit resistance, by "pegging" the expected circuit resistance for a properly functioning ceramic component to a value close to that of the well-known and stable resistor value.

Figure 8C:
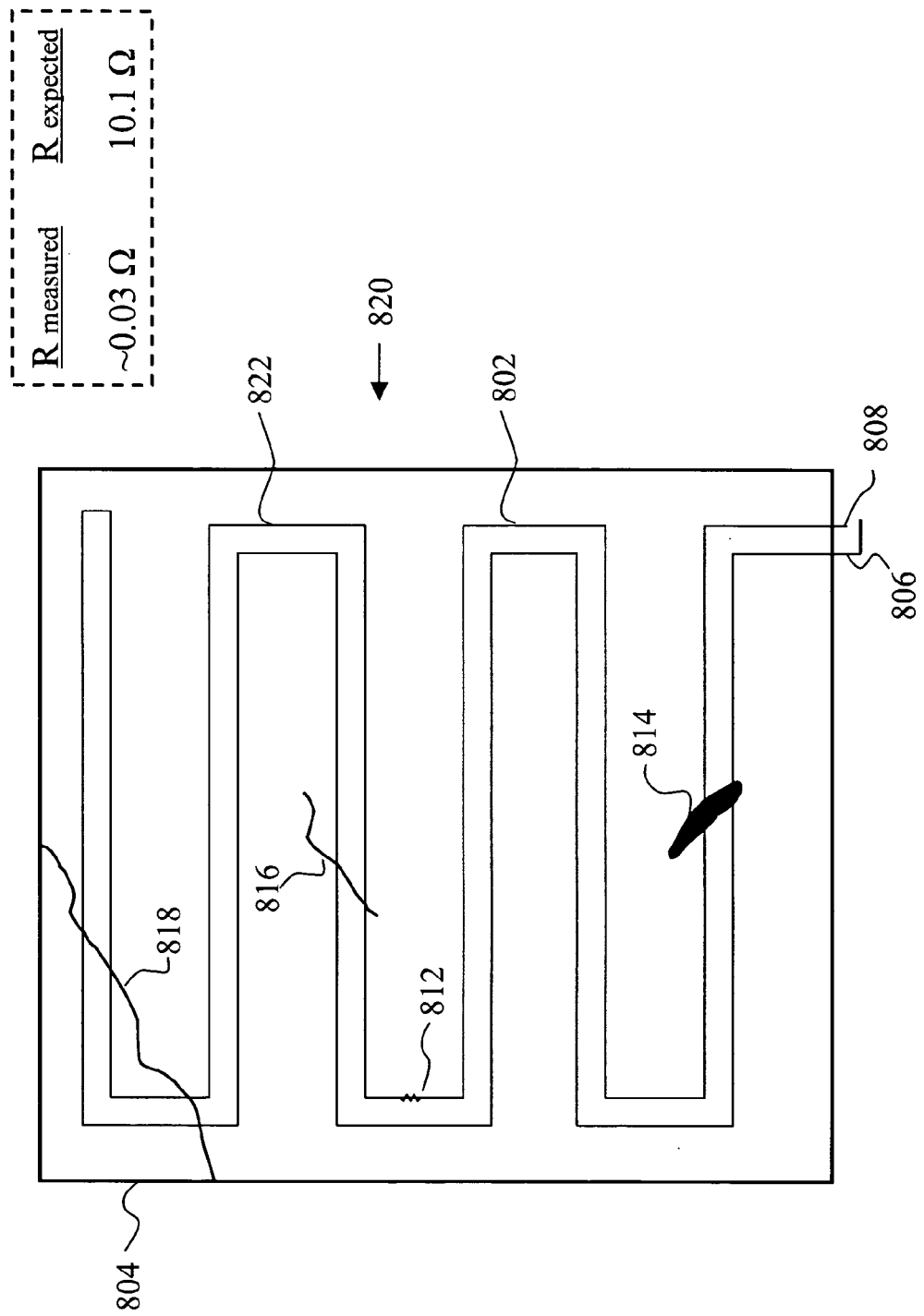
FIG. 8c is a schematic diagram illustrating the effect of simultaneous presence of cracks and a conductive defect on the measurement of a circuit arranged according to another embodiment of the present invention.

In FIG. 8c, system 820 includes circuit 802 with resistor 812 located approximately one-quarter of the distance along the circuit between ends 806, 808. In the example shown, the resistance of resistor 812 is 10 Ω. Accordingly, the total expected resistance of circuit 822, including the residual circuit resistance, is about 10.1 Ω. Therefore, defect 814 located as shown will cause the measured resistance value to be much lower than the expected resistance, in this case, about 0.03 Ω. A user is thus alerted to the fact that a conductive defect is present and may take precautions accordingly. For example, although the user will still not be able to directly determine the presence of cracks 816, 818, which intercept circuit 802 beyond the short circuit point 814, the user is aware of the fact that a short circuit is present, and that cracks in system 820 may accordingly remain undetected. Thus, system 820 may be removed from operation.

Figure 8D:
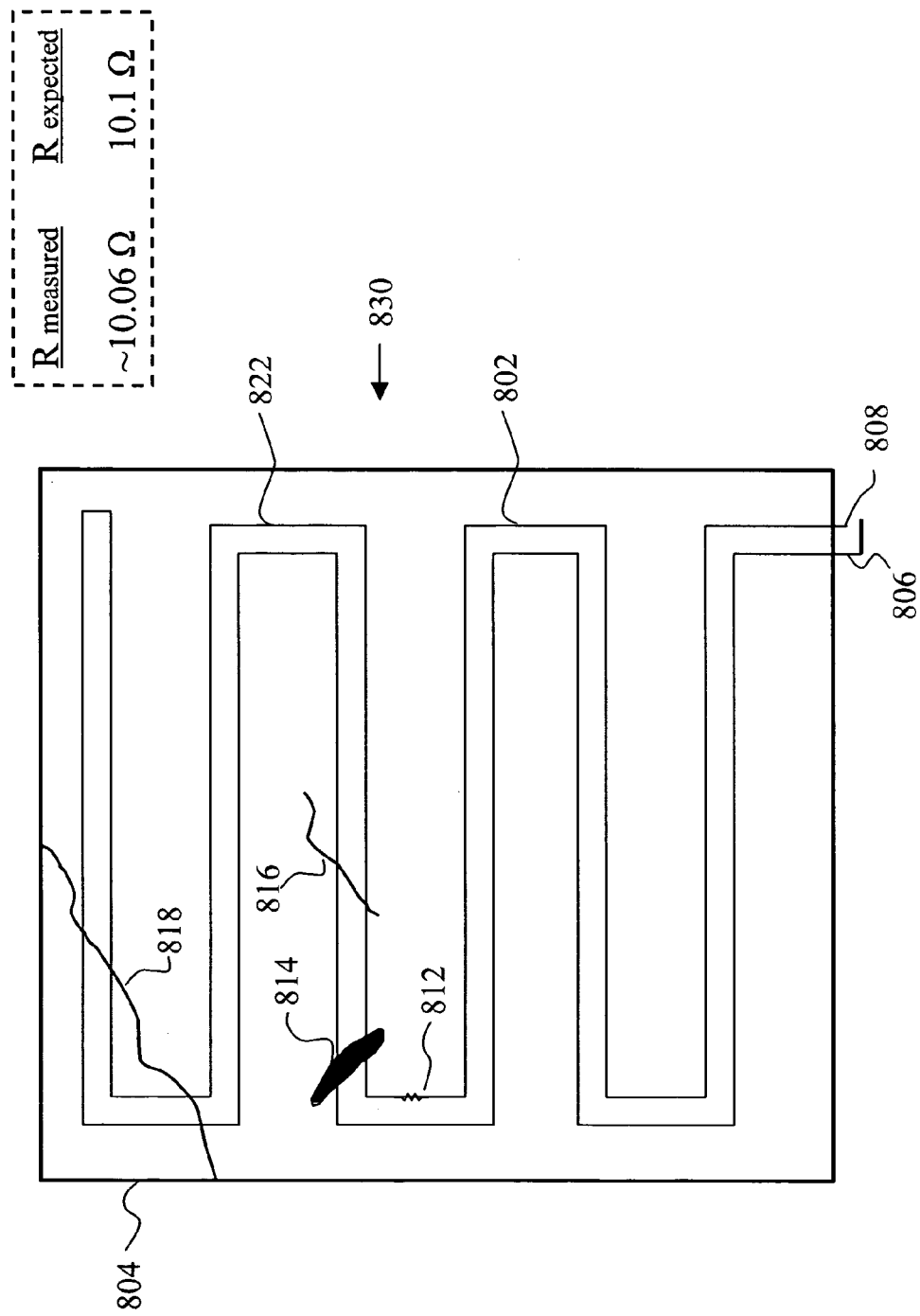
FIG. 8d is a schematic diagram illustrating the effect of a change in location of a conductive defect on a measurement performed on the circuit of FIG. 8c.

FIG. 8d depicts system 830 including circuit 822 with resistor 812 as in FIG. 8c. In this case, conductive defect 814 is located such that it forms a short circuit that includes resistor 812. Thus, a user performing a resistance measurement between points 806 and 808, will measure a value of about 10.06 Ω, which is very close to the expected value of 10.1 Ω. Accordingly, such a measurement will likely produce another false negative interpretation that signifies that system 830 is in working order. Therefore, the presence of cracks 816 and 818, located as shown, will remain undetected.

Figure 8E:
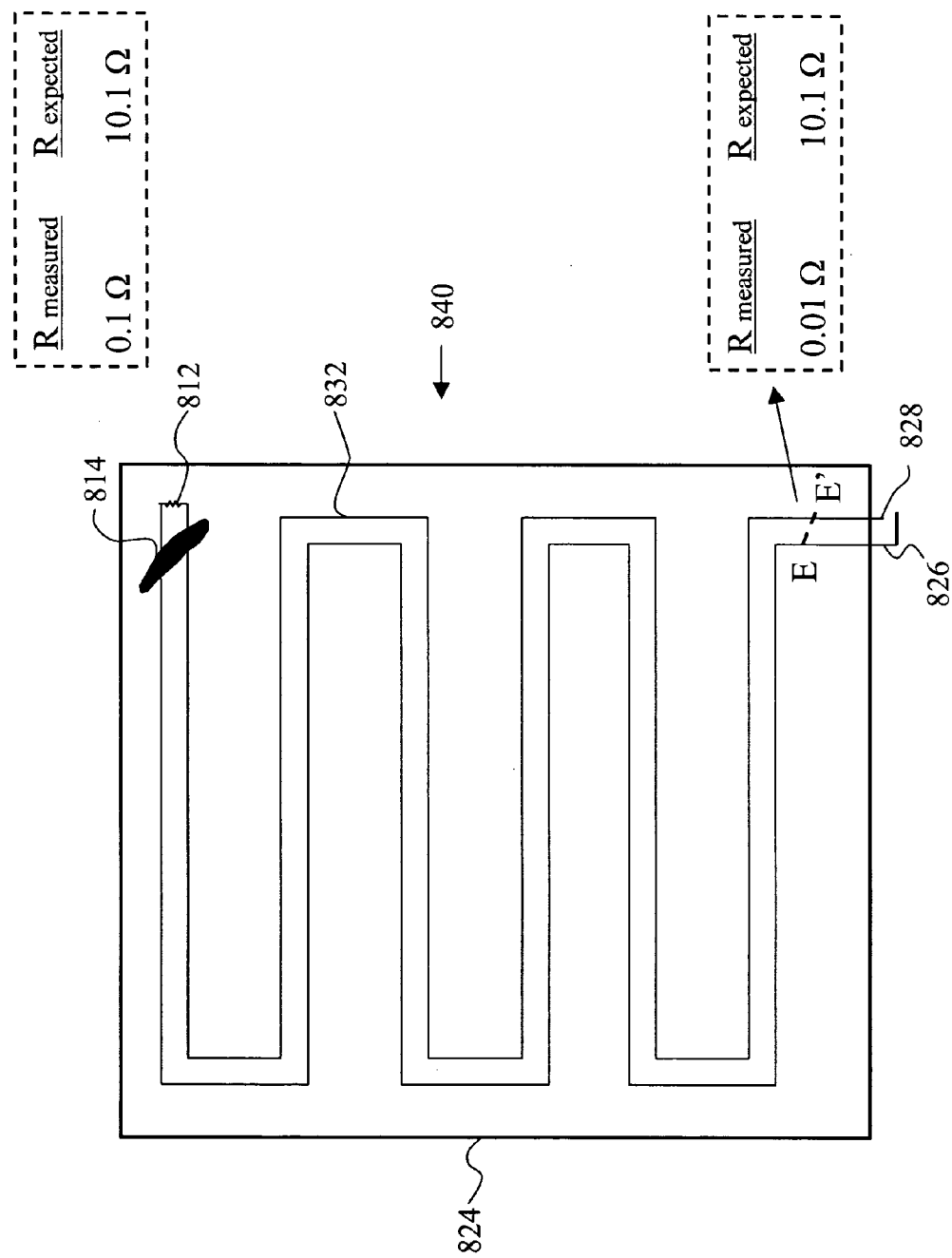
FIG. 8e is a schematic diagram illustrating the effect of a conductive defect on measurement of a circuit arranged according to another exemplary embodiment of the present invention.

FIG. 8e is a schematic diagram illustrating a system 840, arranged according to another exemplary embodiment of the present invention, including circuit 832 with resistor 812 located to minimize the occurrence of false negatives during electrical measurements of the circuit. Resistor 812 is located at about the midpoint of the circuit electrical path between ends 828 and 826. Accordingly, any conductive defect that causes a short circuit will exclude resistor 812. Therefore, a user will in all probability be alerted to the presence of a shorting defect located anywhere on the circuit 832, for example, defect 814 shown in FIG. 8e. System 840 accordingly provides a method for assuring a user of detection of inadvertent shorting defects. Accordingly, since resistor 812 cannot be included within a short circuit, a user measuring an expected circuit resistance of about 10 Ω, is assured that it is not a false negative result, where the presence of cracks in the ceramic are not detected because they lie outside a short circuit.

Although system 840 assures a user of avoiding false negative results, it cannot easily provide a user with information about the location of a shorting defect, if present. In the example illustrated in FIG. 8e, conductive shorting defect 814 is located adjacent to resistor 812 in a corner of ceramic 824. A user accordingly measures a resistance of about 0.1 Ω, the full residual circuit resistance. Were defect 814 to be alternatively located just above ends 826 and 828 between points E–E', the recorded resistance, if accurately measurable, would be about 0.01 Ω. A user would thus be unlikely to distinguish between the two cases. In the latter case, the user would be well advised to remove the system from use, since cracks within the ceramic would remain undetectable. However, in the former case, as illustrated in FIG. 8e, the system will be able to detect cracks positioned almost anywhere in the circuit. However, at least in cases where the circuit is placed at the interface of the ceramic component and a backing, a user measuring a short in system 840, has no way of confidently ascertaining the position of the short. Therefore, system 840 will likely have to be taken out of service because it exhibits a "false positive." The term false positive means, that a conductive defect alerts a user that the system is defective and should not be considered reliable for crack detection, even when it is perfectly capable of so doing, as in FIG. 8e.

Figure 8F:
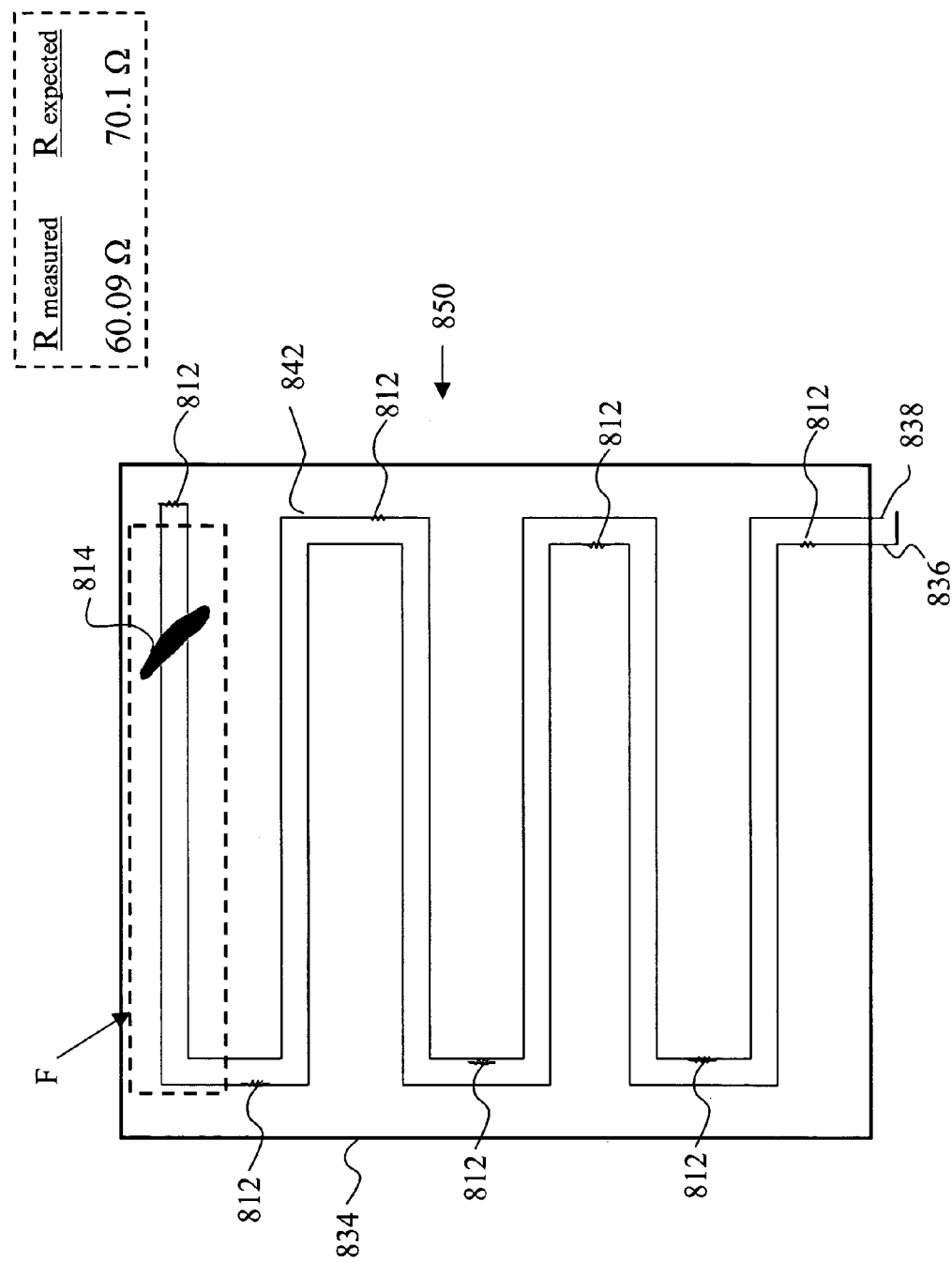
FIGS. 8f and 8g are schematic diagrams illustrating the effect of placement of a conductive defect on measurement of a circuit arranged according to still another exemplary embodiment of the present invention.
Figure 8G:
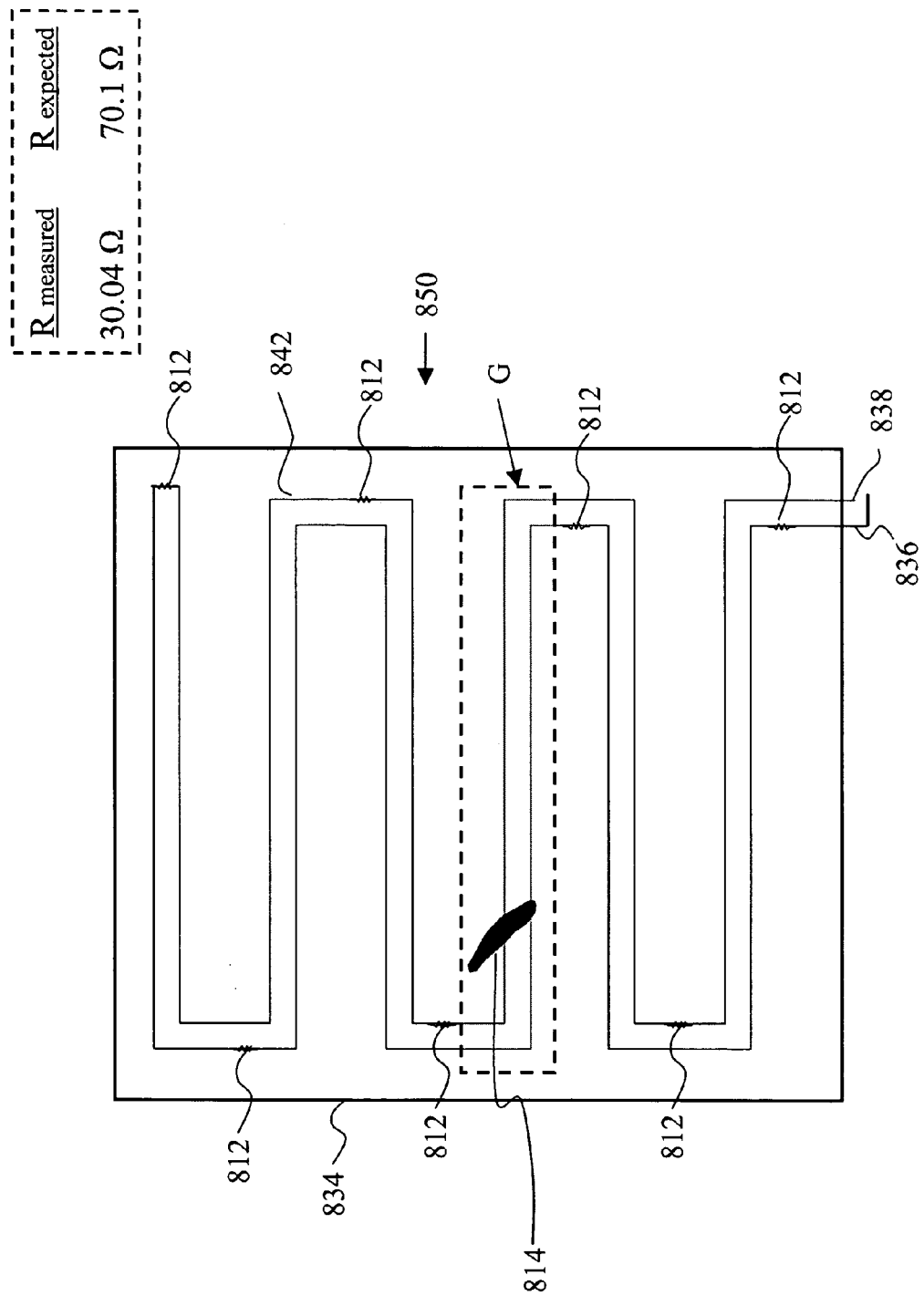

FIG. 8f is a schematic diagram illustrating system 850, arranged according to a preferred embodiment of the present invention, that includes circuit 842 containing multiple resistors located throughout the circuit. Resistors 812, for example, each have about 10 Ω resistance. As illustrated, system 850 includes seven resistors spaced throughout the circuit. A pristine circuit incorporating no conductive defects would exhibit a resistance of approximately 70.1 Ω. An advantage of circuit 842 is that the resistors placed therein are arranged to provide location information to a user as to the position of defects causing short circuits. In the example illustrated in FIG. 8f, neglecting the residual circuit resistance, defect 814 causes the circuit resistance to measure about 60 Ω. The latter value reflects the contribution of six of the resistors 812 in circuit 832 excluding the resistor located at the circuit midpoint, which is no longer included in the short circuit defined by ends 836, 838 and conductive defect 814. It will be apparent to those skilled in the art, that a resistance value of 60 Ω indicates that a conductive defect lies within an area denoted by F in FIG. 8f. Similarly, if conductive defect 814 is located as illustrated in FIG. 8g, the circuit resistance will be measured to be about 30 Ω. In the latter case, since a measured 30 Ω requires that four resistors 812 have been excluded from the circuit, while three resistors remain within the measured short circuit, the user will be reasonably assured that the defect lies within the region denoted by G. It will be further apparent to those skilled in the art, that the location of potential shorting defects can be further narrowed down by the addition of more resistors within a circuit.

Figure 9:
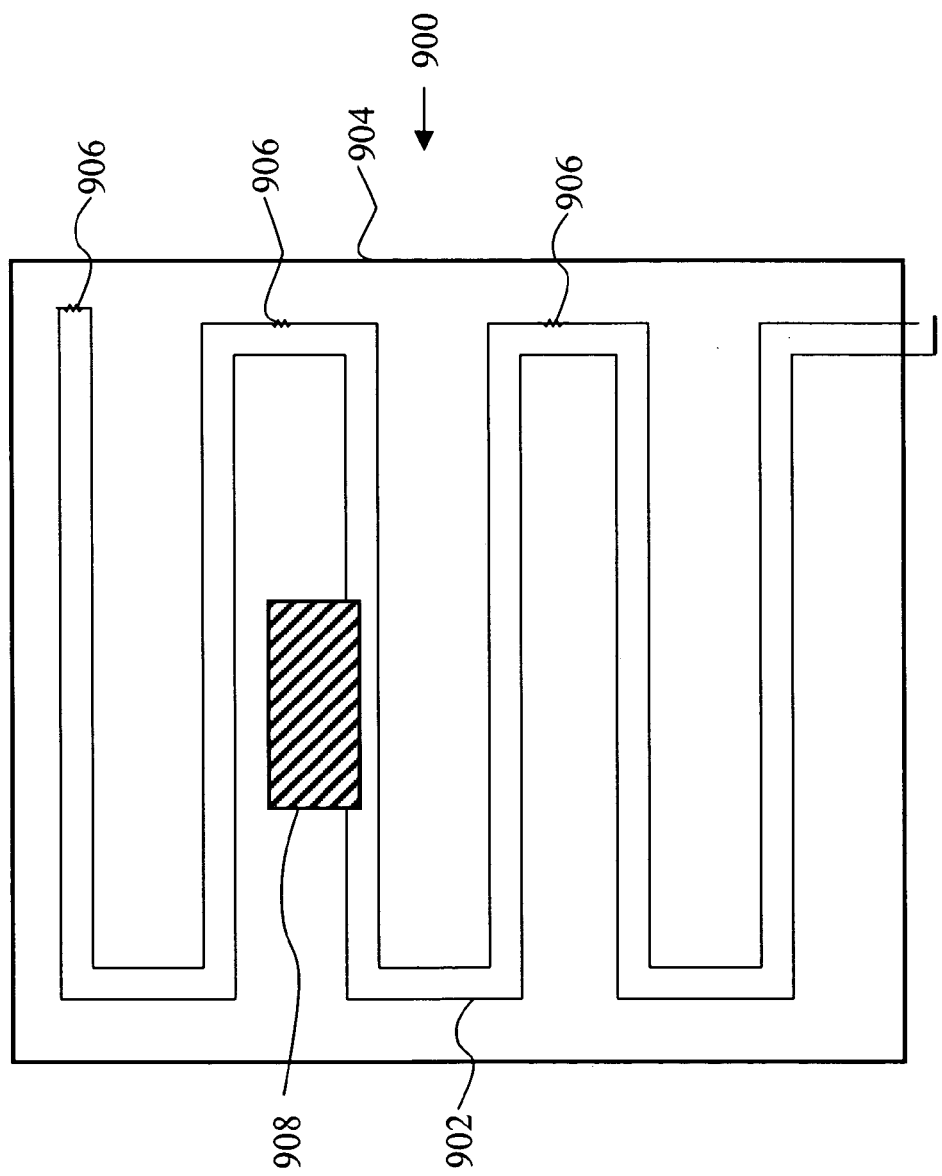
FIG. 9 is a schematic diagram illustrating elements of a ceramic armor system according to a further embodiment of the present invention.

FIG. 9 is a schematic diagram illustrating elements of a ceramic armor system according to a further embodiment of the present invention. In system 900, in addition to an electrical circuit 902 with embedded resistors 906 attached to ceramic component 904, a moisture sensor is placed in contact with circuit 902. The moisture sensor may be one of various known types. The sensor may, for example, be constructed of conducting material whose resistance changes in a controlled manner upon exposure to moisture. In an exemplary embodiment, the resistance of circuit 902 as designed and fabricated is about 50 Ω, including a moisture sensor resistance of about 20 Ω. Upon exposure to substantial moisture the resistance of sensor 908 may increase to about 50 Ω. Accordingly, a user in the field who measures a total circuit resistance of about 80 Ω, may reasonably conclude that the system 900 has been exposed to unwanted moisture, and take steps accordingly.

Although the above discussion has placed emphasis on examples of ceramic crack generation where the cracks are sufficiently wide to generate complete rupture of conductive circuits attached thereto, it is foreseeable that microscopic cracks might generate incomplete disruption of the circuits, such that some degree of electrical conductivity remains. A user may measure a circuit resistance value well in excess of the expected pristine value, but not sufficiently high to indicate a complete circuit break. This may serve to alert the user to incipient or microscopic crack formation or other damage. Thus, embodiments of the present invention may provide information alerting the user to a wide range of possible defects within a ceramic armor component.

The foregoing disclosure of the preferred embodiments of the present invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure. The scope of the invention is to be defined only by the claims appended hereto, and by their equivalents. For example, although embodiments of the present invention with plate-like ceramic components have been described, other component geometries such as cylinders, cubes, and other shapes are envisioned.

Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

What is claimed is:

1. A ceramic armor system with built-in detection of ceramic defects, comprising:
   one or more ceramic components housed within the systems, wherein the one or more ceramic components comprises ballistic impact protection means;
   one or more conductive serpentine circuits, wherein at least one of the ceramic components includes at least one of the conductive serpentine circuits attached directly thereto and providing substantial coverage on at least one first surface of the at least one ceramic component, wherein the one or more conductive serpentine circuits are accessible for electrical measurements; and a plurality of contacts, wherein at least two of the contacts are connected to each conductive serpentine circuit to provide access to a device to measure circuit resistance of the one or more conductive serpentine circuits, wherein cracks and conductive defects in the housed ceramic are detectable.

2. The system of claim 1, wherein the ceramic component comprises a ceramic composite.

3. The system of claim 1, further comprising a backing attached to the ceramic component.

4. The system of claim 1, further comprising at least one resistor incorporated within the one or more conductive serpentine circuits.

5. The system of claim 4, wherein resistance of the at least one resistor is significantly higher than a residual circuit resistance.

6. The system of claim 4, wherein at least one of the conductive serpentine circuits comprises a plurality of resistors arranged to provide location information about conductive defects.

7. The system of claim 1, wherein the plurality of contacts comprise contact pads arranged on the at least one first surface.

8. The system of claim 1, wherein the plurality of contacts comprise integrated connectors configured to receive electrical probes.

9. The system of claim 1, wherein the plurality of contacts comprise side surface contacts, each at least partially disposed on a side surface of a ceramic component, whereby the conductive serpentine circuit disposed on the at least one first surface can be measured by a probe placed on the side surface contact.

10. The system of claim 1, wherein the one or more conductive serpentine circuits is attached to a back surface of a ceramic component.

11. The system of claim 1, wherein the one or more conductive serpentine circuits is attached to a front surface of a ceramic component.

12. The system of claim 1, wherein the ceramic component includes at least one conductive serpentine circuit attached to a front surface and further includes at least one conductive circuit attached to a back surface.

13. The system of claim 1, wherein a plurality of conductive circuits are attached to the first surface.

14. The system of claim 1, further comprising a moisture detector attached to the at least one conductive serpentine circuit.

15. The system of claim 1, further comprising one or more covers, wherein each cover protects a ceramic component and the one or more conductive serpentine circuits attached thereto, and wherein each cover provides access for an electrical measurement of the one or more conductive serpentine circuits.

* * * * *